United States Patent
Gronvall

(12) 
(10) Patent No.: US 7,100,462 B2
(45) Date of Patent: Sep. 5, 2006

(54) SELF ADJUSTING SENSOR MOUNTING DEVICE

(75) Inventor: Daniel Gronvall, Port Angeles, WA (US)

(73) Assignee: BugLab LLC, Danville, CA (US)

( * ) Notice: Subject to any disclaimer, the term of this patent is extended or adjusted under 35 U.S.C. 154(b) by 57 days.

(21) Appl. No.: 10/794,560

(22) Filed: Mar. 5, 2004

(65) Prior Publication Data

US 2005/0193839 A1 Sep. 8, 2005

(51) Int. Cl.
*G01H 1/00* (2006.01)

(52) U.S. Cl. .................................... 73/866.5

(58) Field of Classification Search ............... 73/866.5, 73/61.48, 61.79, 597, 598, 590, 622, 623, 73/627, 629, 865.8; 250/339.11, 341.2, 341.8; 324/228, 229

See application file for complete search history.

(56) References Cited

U.S. PATENT DOCUMENTS

| 4,019,373 A | * | 4/1977 | Freeman et al. ............... 73/644 |
| 4,242,744 A | * | 12/1980 | Rottmar ....................... 367/173 |
| 4,320,659 A |   | 3/1982 | Lynnworth |
| 5,007,291 A |   | 4/1991 | Walters |
| 5,311,785 A | * | 5/1994 | Bar-Shay .................... 73/866.5 |
| 5,585,565 A | * | 12/1996 | Glascock et al. ............. 73/644 |
| 5,644,093 A |   | 7/1997 | Wright |
| 5,767,775 A | * | 6/1998 | Shukla et al. ................ 340/623 |
| RE36,130 E |   | 3/1999 | Haynes |
| 6,337,631 B1 | * | 1/2002 | Pai et al. ..................... 340/618 |
| 6,546,823 B1 | * | 4/2003 | Veit .......................... 73/866.5 |
| 6,622,561 B1 |   | 9/2003 | Lam |

\* cited by examiner

*Primary Examiner*—Robert Raevis

(57) ABSTRACT

A method and device for mounting a sensor to a surface that is flat in one dimension and flat or curved in a second dimension. The mounting method results in stable self-centering attachment of the sensor to the surface across a wide range of radii in the second dimension of the surface. A fixed distance and angle between the sensor components and the surface is automatically maintained despite wide changes in the radius of the surface. An attachment means is provided that is secure, repeatable, and reusable. Additionally, a means of maintaining a clear unobstructed window between the sensor and surface is provided.

35 Claims, 6 Drawing Sheets

SELF ADJUSTING SENSOR MOUNTING DEVICE

CROSS REFERENCE TO RELATED APPLICATIONS

Not applicable.

BACKGROUND

1. Field of the Invention

The present invention relates generally to methods and devices for mounting a sensor securely to variably shaped surfaces. One specific embodiment of the invention relates to mounting a biomass sensor to the external surface of a biofermenter.

2. Description of Prior Art i. Mounting Methods for Non-Invasive Sensors

Non-invasive sensors are widely used in the analysis of material properties. A great advantage of such sensors is that they allow measurements to be made without consuming, infecting, or damaging the material being analyzed. However, for such sensors, maintaining a fixed geometric relationship between the sensor and the material under test is frequently essential to maximizing the accuracy and reproducibility of the measurement. Specifically what is frequently required is to maintain a fixed distance and angle between the sensing components in the sensor, and the surface of the material or the surface of the container holding the material. A particular challenge for sensor mounting is posed when the container holding the material or the material itself is cylindrical in shape, and the radius of the cylinder may vary widely. Prior art has addressed this subject in a variety of ways.

U.S. Pat. No. RE36130—Haynes discloses a method for measuring pipe thickness using a sensor attached to a glide plate that maintains contact with the pipe. The glide plate has a curved underside that matches the shape of the outer surface of the pipe. A manual means of adapting the apparatus for different pipe diameters is provided, but only for a limited range of radii. In addition, the distance between the individual sensor components and the pipe will vary with pipe diameter unless a new glide plate is used for each new pipe diameter.

U.S. Pat. No. 6,622,561—Lam discloses a method of detecting flaws in tubes, employing a sensor mounting pad in one of several possible configurations: (1) the surface of the mounting pad is designed so that it corresponds in shape to the tube, (2) the mounting pad is fabricated from flexible material, or (3) an inflatable component is adjusted to conform the mounting pad to the shape of the tube. The disadvantage of these methods is that they are not automatically adaptable to variable radius surfaces (ie. they requires changing the mounting pad, raising or lowering shoe, or changing the bladder inflation). In addition, this method only provides a means of maintaining a fixed distance between the tube and the entire sensor, as opposed to the individual components in the sensor. As the tube radius is changed, even if a fixed distance is maintained between the tube and the nearest point on the sensor body, the distance between the individual sensor components and the pipe body may change as a result of the changing curvature of the tube.

U.S. Pat. No. 5,007,291—Walters discloses a method of mounting a sensor in close proximity to a pipe in order to inspect its quality. A proximity sensor is used in conjunction with feed-back control and a hydraulic mechanism to maintain a fixed distance between the sensor and the surface of a rotating pipe under inspection. This method has the disadvantage of being cumbersome, complex, expensive, and automatically adaptable to only a narrow range of pipe radii.

U.S. Pat. No. 4,320,659—Lynnworth discloses a system for measuring fluid impedance or liquid level through the wall of a cylindrical container. A method for mounting the sensor is described that maintains floating contact between the sensor and the external wall of the container. The sensor mount is held in place by either magnetic or adhesive means. The methods provided are not automatically adapting to varying radius containers. In addition, the magnetic attachment method provided will only work on steel containers and may be insufficiently secure in high vibration environments. Adhesive attachment is more secure and applicable to a wider array of surfaces, but is not easily removable. Adhesives typically require surface preparation and may fail under constant load. In addition, the use of adhesive would hinder rapid transfer of the sensor between containers, would limit its reusability, and may foul the surface of the vessel being probed.

U.S. Pat. No. 5,644,093—Wright discloses a sensor mounting method employing adhesive pivoting feet that are adaptable to variable radius cylindrical surfaces. In addition, a spring is provided for maintaining contact between the sensor and the mounting surface. The disadvantages associated with the use of adhesive for attachment are described above. The use of pivoting feet reduces the strength of the mounting device and increases the likelihood that the mount could flex or fail in response to force, vibration, or temperature changes. Also, the position of the sensing components within the sensor is not automatically fixed with respect to the mounting surface. Therefore, variation of the radius of curvature of the mounting surface may result in variable distances and angles of the sensor components relative to the surface.

U.S. Pat. No. 4,019,373—Freeman discloses an ultrasonic transducer for sensing flow velocity through a pipe wall. A U-shaped member is used to provide stable mounting of the transducer onto the pipe. Transducer position is adjusted axially by means of a screw thread. The disadvantage of this method is that only a narrow range of pipe radii may be accommodated. In addition, manual adjustment of transducer position is required in order to achieve a fixed distance between the transducer and pipe surface. As a result, the device is not rapidly transferable between pipes, and may be prone to user error, if the transducer position is not carefully adjusted.

U.S. Pat. No. 4,242,744—Rottmar discloses a method of fixing a sonic or ultrasonic transducer to a container for level detection. A spring is used to urge the transducer towards the container. The disadvantage of this method is that no means is provided to maintain a fixed angle between the sensor and the container. As a result, a fixed geometry between the transducer components and container may not be maintained between different placements of the transducer either on the same container or on containers of different size.

ii. Measurement of Biomass in Liquid Cultures

Liquid cultures of cells or microorganisms are frequently grown for research purposes or for commercial gain. Cells or microorganisms can be genetically modified to produce high yields of chemicals that may be difficult, expensive, or impossible to synthesize by other means. In order to prevent growth of other undesirable cells or microorganisms in the same liquid culture, it is important that the culture be grown under sterile conditions. For this reason, the growth medium is sterilized prior to inoculation with the desired cell or microorganism. In order to maintain a barrier to foreign organisms and optimize the growth of the desired cell or microorganism, liquid cultures are frequently grown under highly controlled conditions in what are referred to as fermenters or bioreactors. For research purposes, fermenter vessels are typically cylinders constructed from glass or plastic, having liquid capacities ranging from less than 1 L up to 20 L. For larger scale production, stainless steel tanks with capacities from 10 L up to thousands of liters or more are frequently used. A flat glass port is typically provided on the side of such vessels, to allow for viewing of the liquid culture. In addition to maintaining sterile conditions, fermenters may provide control over such parameters as temperature, pH, rate of stirring, and concentration of nutrients and dissolved gases.

Cells or microorganisms typically undergo several stages of growth in a fermenter. After inoculation, the initial growth rate of the cells or microorganisms may be slow, as the organism becomes accustomed to its new environment. This is frequently followed by a rapid growth phase where the biomass increases nearly exponentially. This growth period is sometimes referred to as the "log phase" due to the fact that the change in the logarithm of biomass is nearly linear with time. Eventually, as the nutrient supply relative to the biomass diminishes, the growth will slow. In order to achieve maximum biomass, the conditions in the fermenter need to be changed during the different phases of growth. Ideally a feedback mechanism would link the measured growth of the cells or microorganisms to the conditions in the fermenter. Frequently, a physical or chemical stimulus is used to induce production of a desired chemical by the cells or microorganisms. The timing of this induction relative to the growth cycle of the cells or microorganisms is often critical in order to achieve maximum chemical yield. Unfortunately, methods of continuously and reliably measuring the growth of cells or microorganisms in liquid cultures are not widely available.

The most commonly used method of measuring the biomass in liquid cultures is by extracting a portion of the liquid and measuring its optical density in a spectrophotometer. This method has several disadvantages: (1) each time liquid is withdrawn, there is a risk that the culture will be contaminated, (2) the method is not continuous, and (3) the method is labor intensive, requiring frequent extraction and precise volumetric dilution of the extracted liquid when high cell concentrations are measured. Commercial devices are available (eg. Wedgewood Technology, Incorporated, Model 650 "Absorbance Monitor") that offer continuous measurement of optical density using a probe that is immersed in the liquid culture. Unfortunately, such devices are prone to drift, particularly due to growth of cells or microorganisms on the sensor itself.

Non-invasive methods of biomass monitoring have also been described in prior art. U.S. Pat. Nos. 5,483,080—Tam and 6,573,991—Debreczeny both describe non-invasive reflectance sensors for measuring biomass in liquid cultures through the wall of a fermenter. By these methods, biomass is measured free from the risk of contaminating the culture. However, sensor mounting methods are not provided that automatically compensate for changes in the shape and size of the fermenter. Due to the wide variety of sizes and shapes of research and production-scale fermenters, external mounting of sensors to the fermenter presents a particular challenge.

SUMMARY OF THE INVENTION

The present invention provides a method and device for mounting a sensor onto a surface that is flat in one dimension and curved or flat in a second dimension. The curvature of the second dimension may vary widely, yet a fixed distance and angle between each of the sensing components and the nearest mounting surface is automatically maintained.

OBJECTS AND ADVANTAGES

Accordingly, several objects and advantages of the present invention are:
a) the sensor mounting method is automatically adaptable to both flat and curved surfaces,
b) a fixed distance and angle is automatically maintained between each of the sensor components and the mounting surface despite changes in the curvature of the mounting surface,
c) the attachment method is easy to use, inexpensive, secure, reproducible, durable and reusable,
d) a means of sealing off the space between the active sensor components and the mounting surface is provided for harsh or dirty environments.

The above-listed advantages of the sensor mounting method result in improved accuracy and reproducibility of the measurements provided by the sensor, and afford greater convenience of use.

Additional objects and advantages of the present invention for the specific embodiment in which a sensor is mounted externally to a fermenter holding a liquid culture for the purpose of measuring the biomass are:
a) the same sensor and mount can be rapidly and reproducibly attached to a variety of different fermenter vessel sizes and shapes; from small-diameter curved glass walls of research-scale vessels to flat glass viewing ports provided on large production-scale vessels,
b) the sensor can be rapidly and reproducibly moved between fermenter vessels without interrupting the growth of the cultures or risking exposure of the cultures to foreign matter.
c) the sensor may be mounted within the viewing aperture provided in heater blankets such as are sometimes used to control the temperature within fermenters.
d) non-metallic materials may be used to avoid damage to glass fermenters, protect against corrosive environments, and reduce the materials costs.

The above-listed advantages result in improved accuracy and convenience of biomass measurements made with the same sensor across a wide range of fermenter types.

Further objects and advantages of the present invention will become apparent from a consideration of the drawings and ensuing description.

Figure 2:
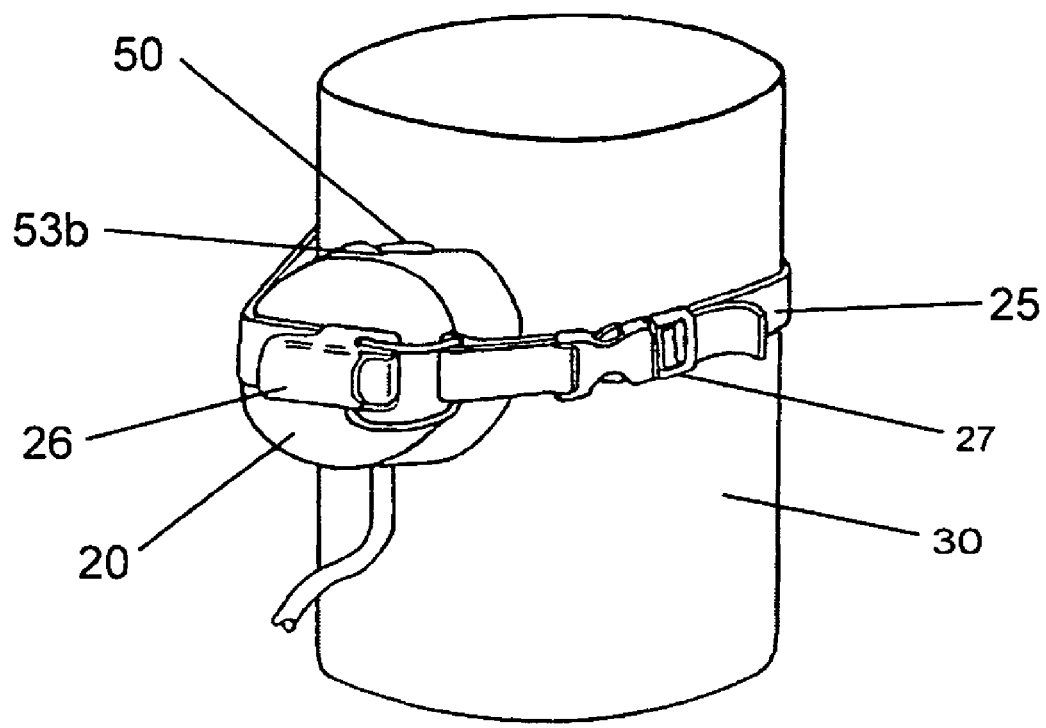
FIG. 2 shows the sensor mounted to the external surface of a vessel.

| Reference Numerals in Drawings | | | |
|---|---|---|---|
| 20 | outer housing | 25 | strap |
| 26 | latch | 27 | buckle |
| 30 | vessel | 40 | flat viewing port |
| 50 | inner housing | 52a | right flat edge |
| 52b | left flat edge | 53a | lower V-notch |
| 53b | upper V-notch | 54 | spring |
| 55 | gasket | 56 | shoulder |
| 57 | o-ring | 58 | central shaft |
| 60 | laser 1 | 61 | laser 2 |
| 62 | sensor cable | 64 | cable slot |
| 66 | inner stop | 68 | outer stop |
| 70 | detector 1 | 71 | detector 2 |
| 72 | sensor face | 73 | sensing window |
| 74 | sensor component plane | 76 | V-notch axis |
| 78 | central mounting axis | 80 | optical axis of laser 1 |
| 82 | platform | 84 | clamp |

DESCRIPTION—PREFERRED EMBODIMENT

Figure 1:
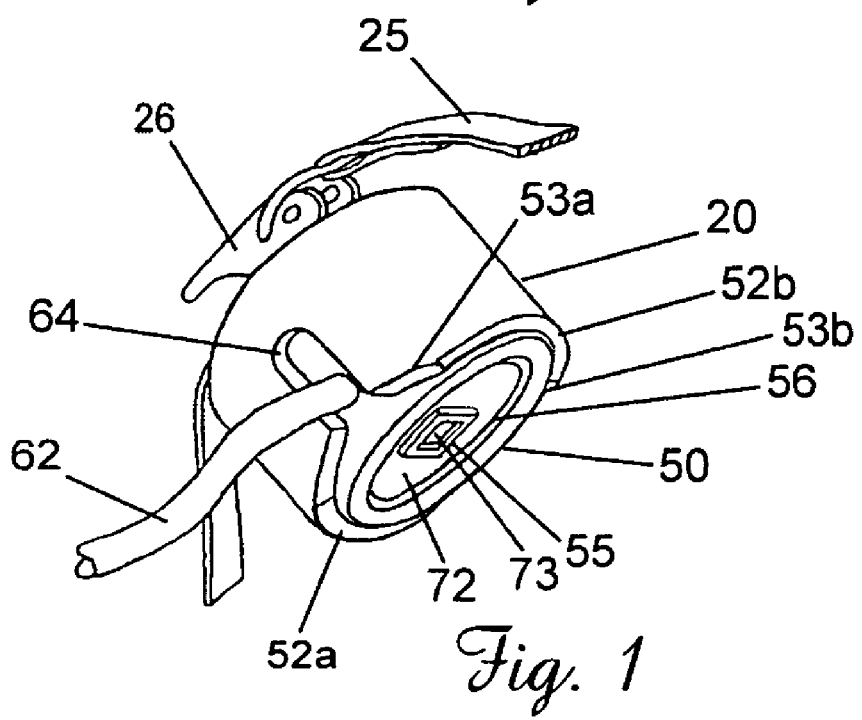
FIG. 1 is a perspective view of a sensor and associated mounting device.

A preferred embodiment of the sensor mount of the present invention is illustrated in FIG. 1. A sensor is held in an inner housing 50 that slides within an outer housing 20. Preferred materials for the construction of the inner and outer housing are light but hard, durable, water- and corrosion-resistant materials such as polyvinylchloride (PVC). Plastic parts may be molded or with minor machining modifications, inexpensive and readily available PVC plumbing end caps may be used for the inner and outer housing, such as 1" and 1¼" endcaps made by NIBCO.

The inner housing of the sensor includes a shoulder 56 and a gasket 55. The shoulder is preferably constructed from a hard, incompressible material, such as PVC, and in the preferred embodiment is simply provided by the edge of the inner housing, as shown in FIG. 1. The gasket is attached by adhesive means to the sensor face 72, surrounding the sensing window 73 of the sensor. The gasket is preferably constructed from a closed-cell compressible material that is water-resistant, such as PVC or polyurethane foam. The sensing window of the sensor is constructed from materials that are at least partially transparent to the radiation or acoustic energy being emitted and detected by the sensor. In the preferred embodiment, this material is transmissive at 850 nm but substantially non-transmissive in the visible region of the spectrum. An example of a suitable material for the sensing window is the plastic optical long-pass filter NT43-948 sold by Edmund Industrial Optics.

The edge of the outer housing 20 has two flat portions 52a and 52b and two V-notched portions 53a and 53b. In addition a slot 64 is provided in the outer housing to allow a sensor cable 62 attached to the inner housing to move along with the inner housing as it slides with respect to the outer housing. A latch 26 is secured to rear of the outer housing. An example of a suitable latch is a ¾" stainless steel toggle latch. The latch is also attached to a strap 25 in two places. An example of a suitable strap material is ¾" nylon webbing.

As shown in FIG. 2, when mounting to a cylindrical surface such as that provided by a vessel 30, the V-notches 53a and 53b of the outer housing 20 are oriented so that they span the curved dimension of the surface. The latch and strap are used in conjunction with a buckle 27 to attach the sensor to the vessel. For example, a ¾" plastic buckle would be suitable. For mounting to larger objects such as production-scale fermentation vessels, an extension strap with male and female buckle components at each end, may be used. The sensor is shown mounted to a production-scale fermentation vessel with a flat viewing port 40 in FIG. 3.

Figure 4:
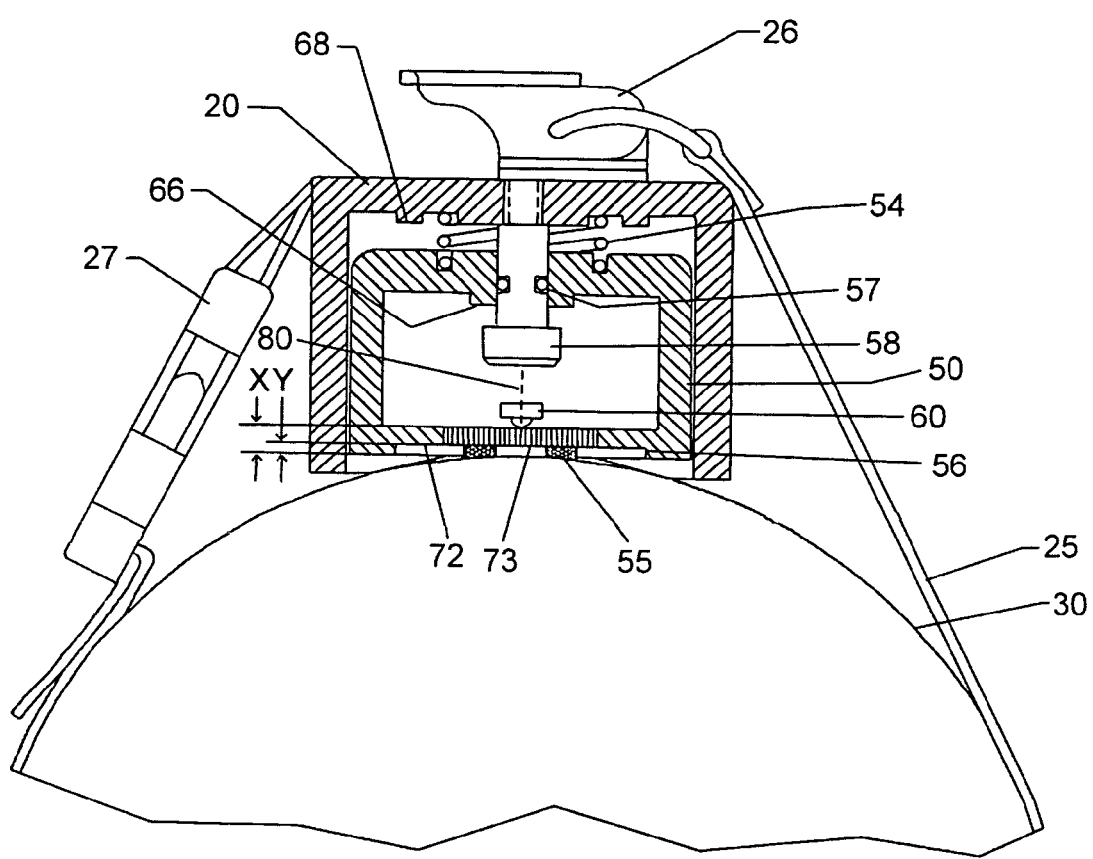
FIG. 4 is a cross-sectional view of the sensor mounted to the external surface of a vessel.

The cross-sectional view provided in FIG. 4 allows for further elucidation of the preferred embodiment of the sensor mount. A central shaft 58 is used to attach the inner housing 50 to the outer housing 20. An example of a suitable central shaft is a ¼"×½" stainless steel shoulder screw modified to include an o-ring seal. Inner 66 and outer 68 stops are provided to limit the range of motion of the inner housing relative to the outer housing. A spring 54 exerts axial pressure on the inner housing towards the surface 30 to which the sensor is attached. The axial force provided by the spring is greater than the force required to compress the gasket 55 on the front face of the sensor onto the mounting surface, but less than the force required to compress the shoulder 56 on the inner housing. An example of suitable choice for spring 54 is a stainless steel spring such as Lee part #LC-055K-1. An O-ring 57 attached to the central shaft 58 is used as a moisture barrier to protect electronic components, such as a laser 60, contained in the inner housing. A example of a suitable O-ring is Parker #2-006 Buna-N.

Figure 6:
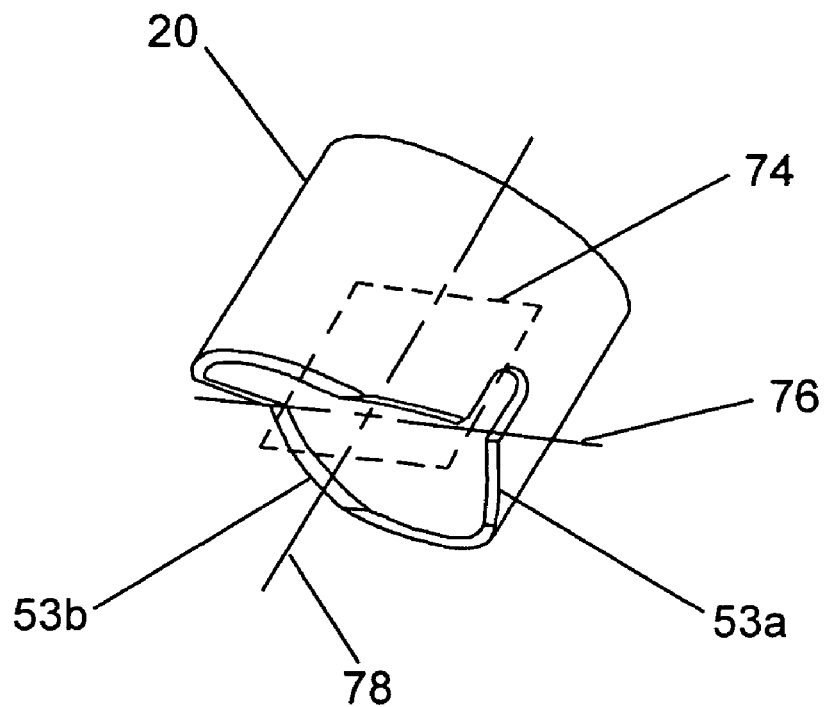
FIG. 6 illustrates the imaginary axes about which the outer housing is self-centering when mounted to a cylindrically shaped surface and the imaginary plane in which the sensor components are positioned.
Figure 7:
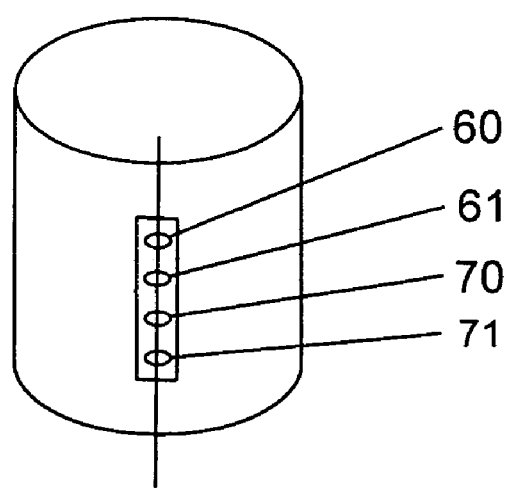
FIG. 7 illustrates the placement of the sensor components relative to the surface to which they are mounted, when the surface is cylindrically shaped.

The sensor within the inner housing contains any number of components capable of emitting and detecting electromagnetic or acoustic radiation. In a preferred embodiment the sensor contains two lasers emitting light at a wavelength of 850 nm, and two detectors sensitive to light at this wavelength. Further details of such a sensor are described in U.S. Pat. No. 6,573,991—Debreczeny, the full text of which is included here by reference. All sensor components are arranged to be included within a single imaginary plane 74 that is illustrated in FIG. 6. This sensor component plane is defined by two axes 76 and 78. The V-notch axis 76 runs through the center of the two V-notches 53a and 53b. The central mounting axis 78 is perpendicular to the front face of the sensor and runs through the center of the V-notch axis 76. When the sensor is mounted to cylindrically shaped surfaces, the intersection of the sensor component plane with the mounting surface is parallel to the flat dimension of the cylinder, as illustrated in FIG. 7. Although the position of each of the sensor components is constrained to be located somewhere within the sensor component plane, the angular orientations of the components are not necessarily constrained to this plane. The angular orientations of the sensor components are determined to maximize the accuracy and reproducibility of the measurement provided by the sensor.

Operation of the Preferred Embodiment

When attaching the sensor to a mounting surface, such as the mounting surface illustrated in FIG. 2, the strap 25 is first wrapped around the circumference of the mounting surface 30. Then the male and female portions of the buckle 27 at the ends of the straps are joined together. The strap can be quickly and easily extended to any length through the use of an extension strap, consisting of an additional length of strap with male and female buckle members attached to the ends. Once the ends of the strap have been buckled together, the excess strap extending from the buckle is pulled in order to tighten the sensor against the mounting surface. This mechanism alone may be sufficient to secure the sensor to the mounting surface. However, in the preferred embodiment, a latch 26 is used to provide additional tensioning force. The tensioning force on the strap needs to be sufficient to compress the spring 54 (FIG. 4), so that the inner housing 50 slides inside the outer housing along the central mounting axis 78 (FIG. 6) compressing the gasket 55 until both the inner and outer housing are in intimate contact with the mounting surface. The preferred embodiment provides a particularly expedient and reproducible method of tensioning the strap: the excess strap is pulled to the extent that the inner housing is held in secure contact with the mounting surface, then the latch is closed, providing a final tensioning force sufficient to secure and center the outer housing onto the surface.

In operation, this method of attachment allows the sensor to be quickly and reproducibly attached and removed from mounting surfaces. In this way the sensor may be used to provide measurements on multiple different surfaces in rapid succession. Alternatively, the sensor may be easily removed and reapplied to the same surface, allowing for cleaning of the surface, for example. By providing a compressible gasket 55 on the sensor face, the preferred embodiment also diminishes the necessity of performing such cleaning operations. The gasket provides a seal against moisture or other contaminants that when introduced between the sensor face and mounting surface, could effect the measurements provided by the sensor. In addition, the gasket provides a means of gripping the mounting surface, thereby reducing the movement of the sensor relative to the mounting surface in high vibration environments. Both of these functions of the gasket have the effect of increasing the accuracy and reproducibility of the measurements provided by the sensor.

The limiting stops provided on the inner and outer housing serve several purposes. The outer stop 68 (FIG. 4) prevents the spring from being over-compressed. Over-compression of the spring may result in a reduction in spring force provided during extension. The outer stop also prevents the shoulder screw from contacting the sensor components or associated electronics. The inner stop 66 determines the limit of extension of the spring. Over-extension of the spring could result in a change in the spring force provided by the spring. The inner stop in combination with the head of the central shaft 58 prevents undesired separation of the inner housing from the outer housing when the sensor is removed from the mounting surface 30.

The O-ring 57 on the central shaft 58 prevents contaminants from entering the inner housing. This function is important in environments where liquid spills are common, since the inner housing contains the sensing components and may contain additional electronic components for controlling the sensor or processing the signals. Additional O-rings or sealants may be applied to the inner housing as further protective measures. In the currently preferred embodiment an additional O-ring is used to seal the junction between the side of the inner housing 50 and the front face 72 of the inner housing. In addition, a silicone adhesive is used to seal the junction between the sensing window 73 and inactive portions of the sensor face 72.

Theory of the Preferred Embodiment

In the preferred embodiment illustrated in FIG. 1, the outer housing 20 is used to provide a stable mounting platform for the sensor held within the inner housing 50. The flat edges 52a and 52b and V-notched edges 53a and 53b of the outer housing provide stable mounting surfaces for both flat and cylindrical surfaces. When mounting to a cylindrical surface, the V-notches will accommodate a wide range of cylinder sizes. For example the currently preferred embodiment accommodates all diameters larger than 2", including flat surfaces. Smaller diameter surfaces could be easily accommodated by altering the V-notch angle and depth. The two V-notches also provide the benefit of automatically centering the sensor about the V-notch axis 76 and the central mounting axis 78, illustrated in FIG. 6.

The force exerted on the V-notches by strap tensioning during attachment to a cylindrical surface will cause the outer housing to rotate about the central mounting axis 78 (FIG. 6) until the V-notches span the curved dimension of the cylinder. The effect of this self-centering mechanism is to align the intersection of the sensor component plane 74 with the mounting surface 30 along the flat dimension of the mounting surface, as illustrated in FIG. 7.

The force exerted between the V-notches and a cylindrical surface during mounting also causes the outer housing to center about the V-notch axis 76 (FIG. 6). Since the sensor components are arranged within a plane 74 that includes this axis, the result is that the angle subtended by the center axis of each of the sensor components and the imaginary tangential line emanating from the nearest point on the mounting surface is independent of the radius of curvature of the mounting surface. What is meant by the center axis of each sensing component is, in the case of sources, the center of the beam of emitted energy or sound, and in the case of detectors, the center of the cone in which the detector is sensitive to incoming energy or sound. For example, in FIG. 4, the angle subtended by the center optical axis 80 of the laser 60 and the tangent to the closest point on the mounting surface is zero degrees. Changing the curvature of the cylinder will not affect this angle.

Figure 3:
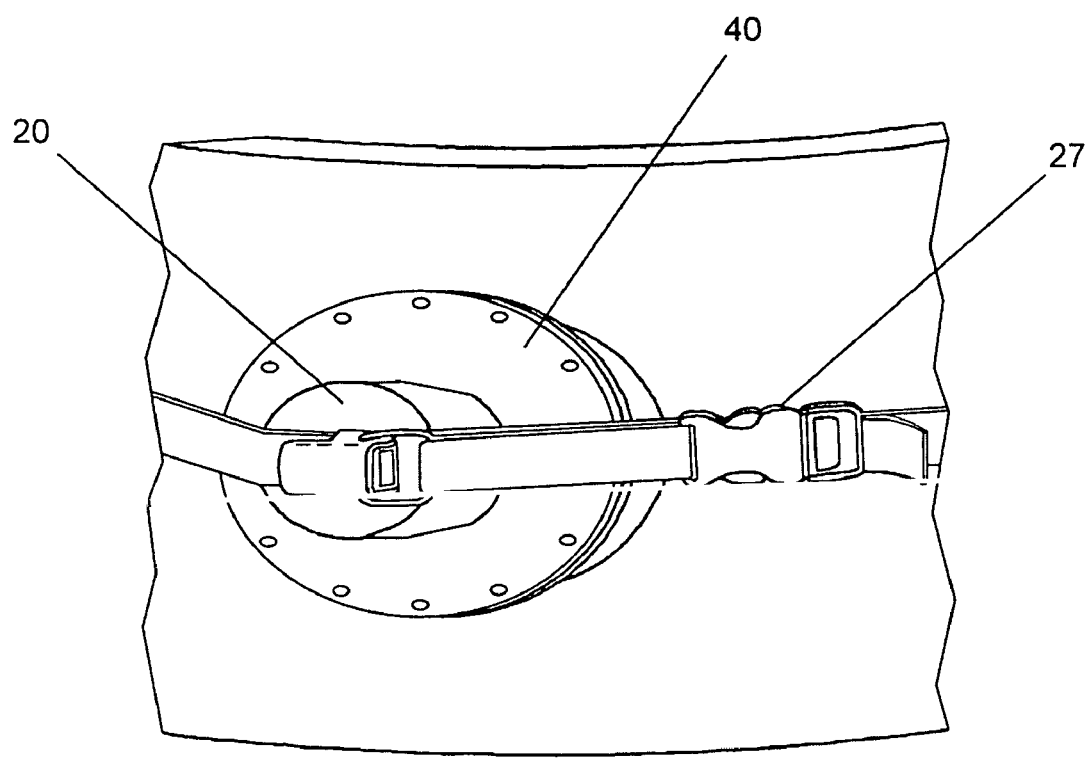
FIG. 3 shows the sensor mounted to a vessel having a flat viewing port.
Figure 5:
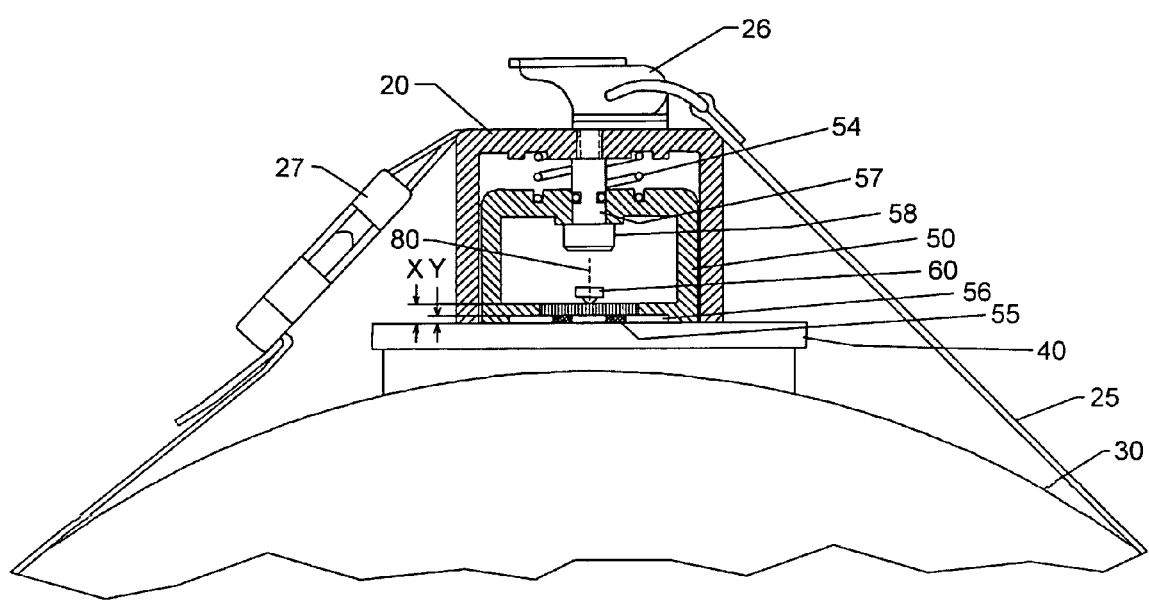
FIG. 5 is a cross-sectional view of the sensor mounted to the flat viewing port of a vessel.

When mounting the same sensor to a flat surface, such as shown in FIGS. 3 and 5, the flat edges of the outer housing 52a and 52b (FIG. 1) provide a stable surface for mounting. As seen in FIG. 5, the angle between the center optical axis 80 of the laser and the surface tangent is still zero degrees when the mounting surface is flat.

The sensor mounting method of the present invention also provides a means of automatically fixing the distance between each of the sensor components and the nearest point on the mounting surface. When applying the sensor to a surface, the spring 54 (FIG. 4) applies sufficient force to compress the gasket 55 but not the shoulder 56 of the inner housing onto the face of the mounting surface. The height of the shoulder 56 thus establishes the distance between each of the sensor components and the mounting surface. When the mounting surface is either cylindrical or flat in shape, the line defining the shortest distance between any of the sensor components and the mounting surface will lie within the sensor component plane 74 (FIG. 6). This distance will be independent of the curvature of the mounting vessel. FIGS. 4 and 5 illustrate this point. In FIG. 4, the sensor is mounted directly to a cylindrical surface with steep curvature. The distance X between the laser 60 and the nearest point on the mounting surface is determined by the height Y of shoulder 56, and by the placement of the laser within the inner housing. As the curvature of the cylindrical surface is decreased or increased, the distances X and Y will be unchanged. This is illustrated at one extreme in FIG. 5, where the mounting surface is now flat, but X and Y are the same as in FIG. 4.

Additional Embodiment

In an additional embodiment of the present invention, the shoulder 56 (FIG. 1) on the inner housing is adjustable. The height of the shoulder is raised or lowered relative to the sensor face 72 by providing a part separate from the rest of the inner housing whose separation from the inner housing is adjustable by a screw or similar means. Alternatively, set screws are used in place of the shoulder—the height of the set screws would thus replace the function of the shoulder. In yet another alternative, variable width spacers are added to or removed from the inner housing of the sensor to vary the height of the shoulder.

The operational advantage conferred by these embodiments are apparent when the distance between the sensor and an inner surface of a container is critical to the accurate functioning of the sensor. In such cases, if the thickness of the container (ie. the distance between the inner and outer surfaces) is variable, changing the height of the shoulder will provide a means of compensating for this variation. The benefits of providing a variable distance between a sensor and a mounting surface are further described in U.S. Pat. No. 6,573,991—Debreczeny.

In another embodiment of the present invention, a means of achieving a predetermined angle between the sensor components and the mounting surface is provided. In one embodiment, a nest is provided for the sensor components that is adjustable so that all of the components are tilted in concert. Alternatively individually adjustable pockets are provided for each or certain of the sensor components. In one embodiment the method of adjusting either the entire ensemble of components or each of the individual components is by rotation of screws positioned to allow tilting in orthogonal planes. In another embodiment, the entire nest of components or the individual components are supported on at least one rotatable column. In a further embodiment, the rotatable column or columns are adjusted in predefined increments resulting in reproducible adjustment of the angular setting.

Alternative Embodiments

Many alternatives to the metal spring 54 provided in the preferred embodiment are also capable of providing the desired function. In one embodiment, a plastic or other non-metallic spring is used. In another embodiment a leaf spring is used instead of a coiled spring. In yet other embodiments an elastic gel, an elastic liquid bladder, or a pneumatic cylinder is used to provide the desired force.

In one alternative embodiment of the present invention, the spring 54 limits the range of motion of the inner housing 50 within the outer housing 20. In this embodiment the inner 66 and outer stops 68 are unnecessary. In other alternative embodiments, the spring limits the range of motion at one extreme of travel along the central mounting axis 78 (FIG. 6) while a physical stop is employed at the other extreme of travel.

For applications where it is desirable that the sensor travels along the mounting surface, an embodiment is provided in which the shoulder 56 is replaced by wheels or bearings. In addition to determining the distance between the surface and the sensor components, the wheels or bearings would allow the sensor to move across the surface with reduced friction. For this embodiment, the strap 25 is not applied directly to the mounting surface but to a support structure that both holds and rotates the cylindrical mounting surface.

Figure 8:
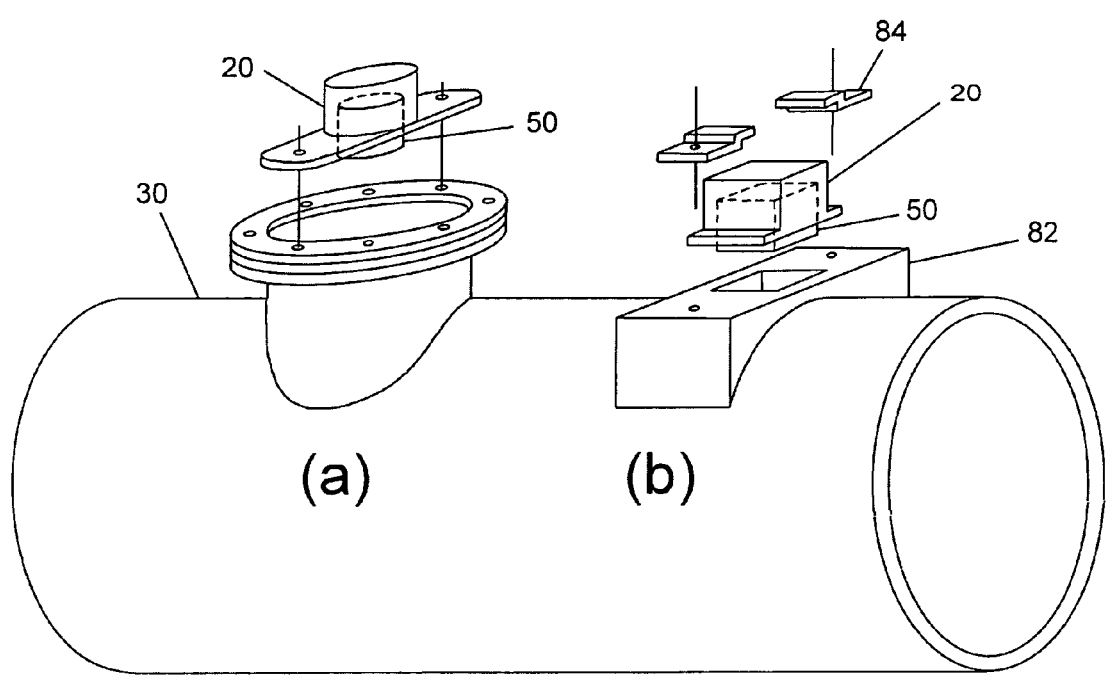
FIG 8 shows perspective views of sensors and associated mounting devices that do not require a strap.

Many alternatives to the strap method of securing the sensor to the mounting surface are applicable to certain applications of the present invention. In one embodiment, the outer housing is secured to the surface with adhesive. Alternative embodiments are illustrated in FIG. 8. In FIG. 8a platform 82 is permanently or semi-permanently attached to the mounting surface 30 by welding, screwing, gluing, application of adhesive tape, or similar methods. The outer housing 20 and inner housing 50 are mounted to the surface by application of clamps 84 between the outer housing and platform. As the clamps are screwed down, the inner housing slides within the outer housing in the same fashion as described for the preferred embodiment. In the alternative embodiment illustrated in part a of FIG. 8, the clamps 84 are screwed directly into the mounting surface, eliminating the need for a platform.

APPLICATIONS

Examples of applications for which the sensor mounting method of the present invention may provide benefits are next described. This is not meant as an exhaustive list, but merely as a sampling of the many possible areas of application:
  (1) non-invasive biomass monitoring
  (2) pipe surface flaw detection
  (3) pipe thickness measurement
  (4) pipe weld quality control
  (5) non-invasive fluid level measurement
  (6) non-invasive fluid impedance measurement
  (7) waste/septic management
  (8) chemical liquid material processing
  (9) nuclear fuel and control rod measurement
  (10) military ordinance monitoring, including:
    a. fuel level sensing during or after assembly
    b. attachment/detachment sensing on aircraft
  (11) fuel cell sensing
  (12) food processing (ingredient levels, flow rate, etc.)
  (13) column chromatography sensing

CONCLUSION, RAMIFICATIONS, AND SCOPE

Accordingly, this invention provides a stable means of mounting a sensor to both cylindrical and flat surfaces in a manner that is self-compensating for the curvature of the mounting surface. This self-compensating mechanism allows the source and detection components in the sensor to maintain a fixed geometric relationship with the nearest mounting surface, independent of its radius of curvature. The result is increased accuracy and reproducibility of the measurements provided by the sensor. Furthermore, the sensor mounting method is easy to apply, reproducible, reusable, and inexpensive.

Although the description above contains many specificities, these should not be construed as limiting the scope of the invention but as merely providing illustrations of some of the presently preferred embodiments of this invention. Many variations are possible. For example:
  the V-shaped notches on the outer housing are replaced with U-shape notches
  the latch may be eliminated from the strapping mechanism the gasket is constructed from alternate materials such as to provide gas-tight instead of water-tight protection or to function in high temperature environments.

the gasket is omitted metallic materials are used instead of plastic ones additional shafts are added to increase stability the central shaft is eliminated the sensing window of the sensor is removed Thus the scope of the invention should be determined by the appended claims and their legal equivalents, rather than by the examples given above.

The invention claimed is:

1. A device for attaching a sensor to an external surface of a vessel, said sensor non-invasively sensing a property related to the concentration of constituents in said vessel, said external surface being substantially flat in a first dimension and curved or flat in a second dimension, comprising:
   a) an inner housing containing said sensor, said sensor including at least one component emitting electromagnetic radiation and at least one component detecting electromagnetic radiation, wherein the sensor components are disposed within a plane that is parallel to said first dimension of said external surface when the sensor is mounted to the vessel;
   b) an outer housing providing a means of stably mounting said sensor to said vessel that automatically accommodates a wide range of variable radii of said second dimension of said external surface when said second dimension of said external surface is curved, and is substantially self-centering about at least one axis with respect to said external surface when said second dimension of said external surface is curved;
   c) a means of attaching said inner housing to said outer housing that self-adjusts to different radii of said second dimension of said external surface when said second dimension of said external surface is curved, wherein a fixed geometric relationship is maintained between each of the sensor components and nearest points on a chosen surface of said vessel,
whereby said sensor is stably attached to a wide variety of vessels in a manner that provides automatic compensation for the curvature of the external surfaces of said vessels.

2. The device of claim 1 wherein said means of stably mounting includes a V-notched shape in said outer housing.

3. The device of claim 1 wherein said means of stably mounting includes a U-notched shape in said outer housing.

4. The device of claim 1 wherein said means of attaching said inner housing to said outer housing includes a spring.

5. The device of claim 1 wherein said fixed geometric relationship includes at least one predetermined distance between at least one of said sensor components and the nearest point on said chosen surface.

6. The device of claim 5 including a means of adjusting at least one said predetermined distance between said sensor components and said chosen surface.

7. The device of claim 1 wherein said fixed geometric relationship includes at least one predetermined angle between at least one of said sensor components and the nearest point on said chosen surface.

8. The device of claim 7 including a means of adjusting said predetermined angle between said sensor components and said chosen surface.

9. The device of claim 1 wherein one of the self-centering axes is perpendicular to the mounting surface.

10. The device of claim 1 wherein one of the self-centering axes is parallel to said first dimension of said surface.

11. The device of claim 1 wherein said chosen surface is the external surface of said vessel.

12. The device of claim 1 wherein said chosen surface is the internal surface of said vessel.

13. The device of claim 1 wherein said outer housing is mounted to said external surface by means of a strap looped around the circumference of said vessel.

14. The device of claim 13 providing an additional strap as a means of extending the length of the first said strap.

15. The device of claim 13 including at least one means of applying tension to said strap so that said sensor is fixedly and reproducibly secured to said external surface.

16. The device of claim 15 wherein said means of applying tension comprises a first means of loosely tensioning said strap onto said external surface and a second means of tightly tensioning said strap onto said external surface.

17. The device of claim 16 wherein said first means is a buckle and said second means is a latch.

18. The device of claim 1 wherein a material that is transparent to said radiation is used to fill a gap between said sensor and said external surface.

19. The device of claim 18 wherein said material is an index-matching gel.

20. The device of claim 1 wherein said vessel is part of a fermenter or bioreactor.

21. The device of claim 1 wherein said sensor components are arranged so that reflectance from the interior of a fermenter or bioreactor is measured.

22. The device of claim 21 wherein said concentration of constituents is related to the biomass in said fermenter or bioreactor.

23. The device of claim 1 wherein at least one said component emitting electromagnetic radiation emits light in the near infrared region of the spectrum.

24. The device of claim 1 wherein said inner housing includes both a compressible member and an incompressible member that surround a face of said device, arranged such that when said device is attached to said external surface, said compressible member is compressed until said incompressible member contacts said external surface, thereby providing a seal between said external surface and said face of said device without affecting said fixed geometric relationship.

25. The device of claim 24 wherein said compressible member also provides a means of gripping the mounting surface.

26. The device of claim 1 wherein a means is provided for sealing said inner housing against the surrounding environment.

27. The device of claim 1 wherein said outer housing is attached to said external surface using adhesive.

28. The device of claim 1 wherein a permanent fixture is attached to said external surface, said fixture providing a means of securely attaching said outer housing to said external surface.

29. A method of attaching a sensor to an external surface of a vessel, said sensor non-invasively sensing a property related to the concentration of constituents in said vessel by means of at least one component emitting electromagnetic radiation and at least one component detecting electromagnetic radiation, said external surface being substantially flat in a first dimension and curved or flat in a second dimension, which comprises the steps of:
  a) surrounding said vessel with a strap that is attached to an outer housing, said outer housing also being attached to an inner housing containing said sensor;
  b) forming a closed loop around said vessel comprising said strap and said outer housing, by a means that does not require the use of tools;
  c) tensioning said closed loop by a means that is rapid and reproducible and does not require the use of tools, thereby urging both said outer housing and said inner housing against said external surface, thereby resulting in:
    (1) said outer housing stably mounting said sensor to said vessel with automatic accommodation for a wide range of variable radii of said second dimension of said external surface when said second dimension of said external surface is curved, and self-centering said sensor about at least one axis with respect to said external surface when said second dimension of said external surface is curved, wherein the sensor components are disposed within a plane that is parallel to said first dimension of said external surface, and
    (2) said inner housing self-adjusting to different radii of said second dimension of said external surface when said second dimension of said external surface is curved, wherein a fixed geometric relationship is maintained between each of the sensor components and nearest points on a chosen surface of said vessel, whereby said sensor is stably attached to a wide variety of vessels in a manner that provides automatic compensation for the curvature of the external surfaces of said vessels.

30. The method of claim 29 wherein said closed loop is formed using a buckle.

31. The method of claim 30 wherein said tensioning of said closed loop is performed by a method that includes pulling said strap through said buckle.

32. The method of claim 31 wherein said tensioning of said closed loop is performed by a method that further includes closing a latch.

33. The method of claim 29 wherein said vessel is part of a fermenter or bioreactor.

34. The method of claim 33 wherein said concentration of constituents is related to the biomass in said bioreactor or fermenter.

35. The method of claim 29 wherein said inner housing includes both a compressible member and an incompressible member that surround a face of said inner housing, arranged such that when said inner housing is attached to said external surface, said compressible member is compressed until said incompressible member contacts said external surface, thereby providing a seal between said external surface and said face of said inner housing without affecting said fixed geometric relationship.

* * * * *